US00PP16490P2

(12) United States Plant Patent
Monet

(10) Patent No.: US PP16,490 P2
(45) Date of Patent: May 2, 2006

(54) NECTARINE TREE 'S 6817'

(50) Latin Name: *Prunus persica*
Varietal Denomination: S 6817

(75) Inventor: René Francois Monet, Villenave d'Ornon (FR)

(73) Assignee: Agri-Obtentions SA, Guyancourt Cedex (FR)

( * ) Notice: Subject to any disclaimer, the term of this patent is extended or adjusted under 35 U.S.C. 154(b) by 75 days.

(21) Appl. No.: 10/642,441

(22) Filed: Aug. 14, 2003

Related U.S. Application Data

(60) Provisional application No. 60/404,173, filed on Aug. 15, 2002.

(51) Int. Cl.
*A01H 5/00* (2006.01)

(52) U.S. Cl. ..... Plt./190

(58) Field of Classification Search ..... Plt./190
See application file for complete search history.

(56) References Cited

U.S. PATENT DOCUMENTS

PP11,968 P2 * 7/2001 Bradford ..... Plt./190

* cited by examiner

*Primary Examiner*—Anne Marie Grunberg
*Assistant Examiner*—June Hwu
(74) *Attorney, Agent, or Firm*—Stratton Ballew PLLC

(57) ABSTRACT

A new cultivar of nectarine tree (*Prunus persica* L. Batsch) named 'S 6817' is dislosed. The fruit of 'S 6817' is oblate, yellow fleshed, and semi-freestone.

5 Drawing Sheets

Latin name of the genus and species of the plant claimed: *Prunus persica* L. Batsch.
Variety denomination: 'S 6817'.

BACKGROUND OF THE INVENTION

The new nectarine tree 'S 6817' was developed by the Institut National de la Recherche Agronomique (INRA) at Angers, France, as part of a controlled breeding program. 'S 6817' was one of several seedlings resulting from a cross of [(Kiang-Si×Independece)×Summergrand]×Marsun (all unpatented). 'S 6817' was asexually propagated by budding at Angers, France, and has been observed to remain true to type over successive asexually propagated generations.

BRIEF SUMMARY OF THE INVENTION

'S 6817' was selected for its suitability as a commercial nectarine tree cultivar. Fruit of the 'S 6817' cultivar matures in late August in central Washington state, and is notable for its oblate shape. The fruit of 'S 6817' is distinguishable from that of the parent varieties by its oblate shape and smooth skin. The characteristics which distinguish 'S 6817' from its parents are set forth in Table 1.

TABLE 1

| Variety | Fruit Type | Shape | Flesh Color |
|---|---|---|---|
| S 6817 | Nectarine | Flat | Yellow |
| Kiang-Si | Peach | Flat | Yellow |
| Independence | Nectarine | Round | Yellow |
| Summergrand | Nectarine | Round | Yellow |
| Marsun | Peach | Round | Yellow |

This variety is distinguishable over related variety 'S 6816' (U.S. patent application Ser. No. 10/642,442) by its later maturity date and larger and slightly astringent fruit.

BRIEF DESCRIPTION OF THE PHOTOGRAPHS

DETAILED BOTANICAL DESCRIPTION OF THE VARIETY

Figure 1:
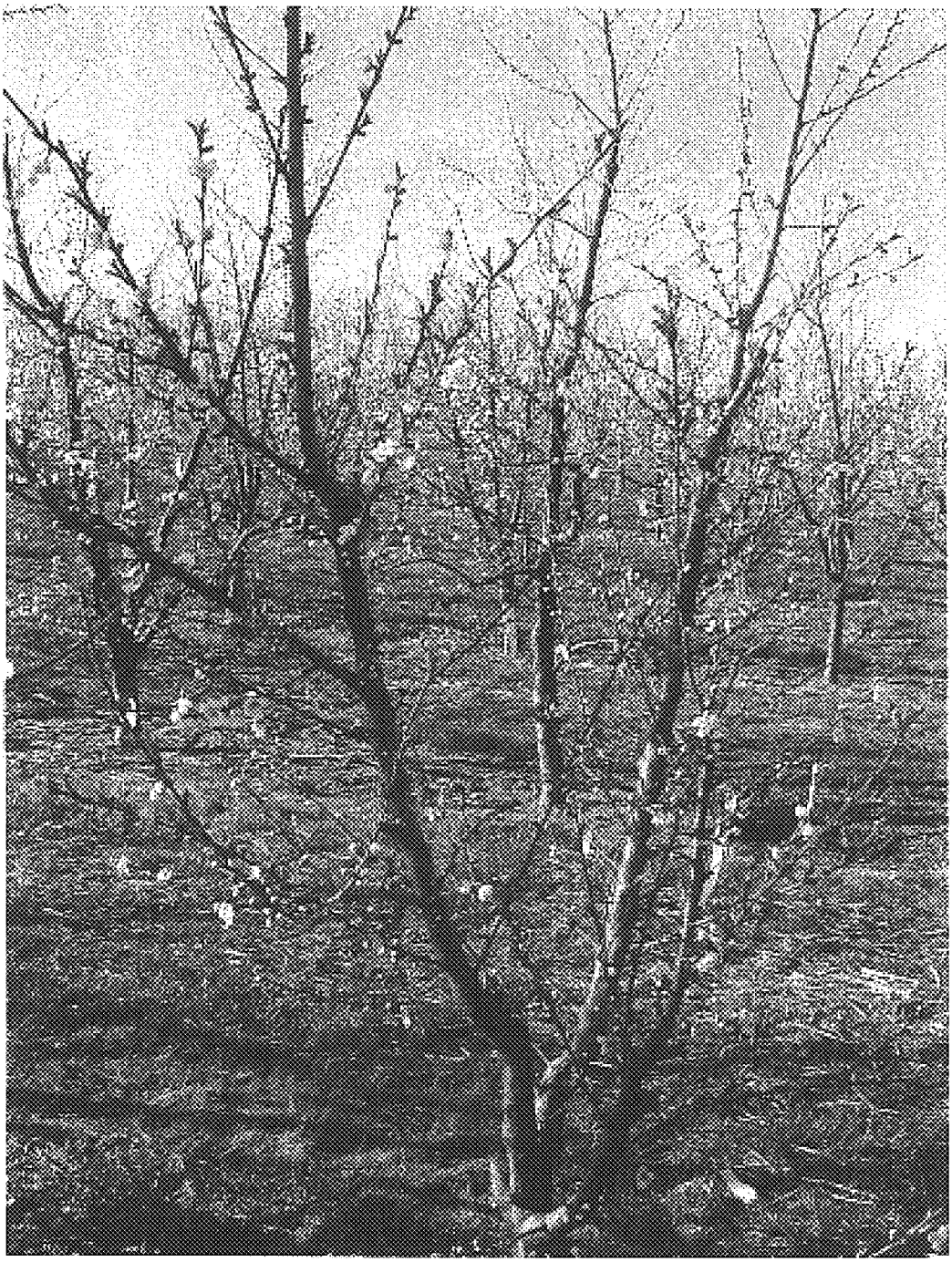
FIG. 1 shows a tree of the new cultivar.
Figure 2:
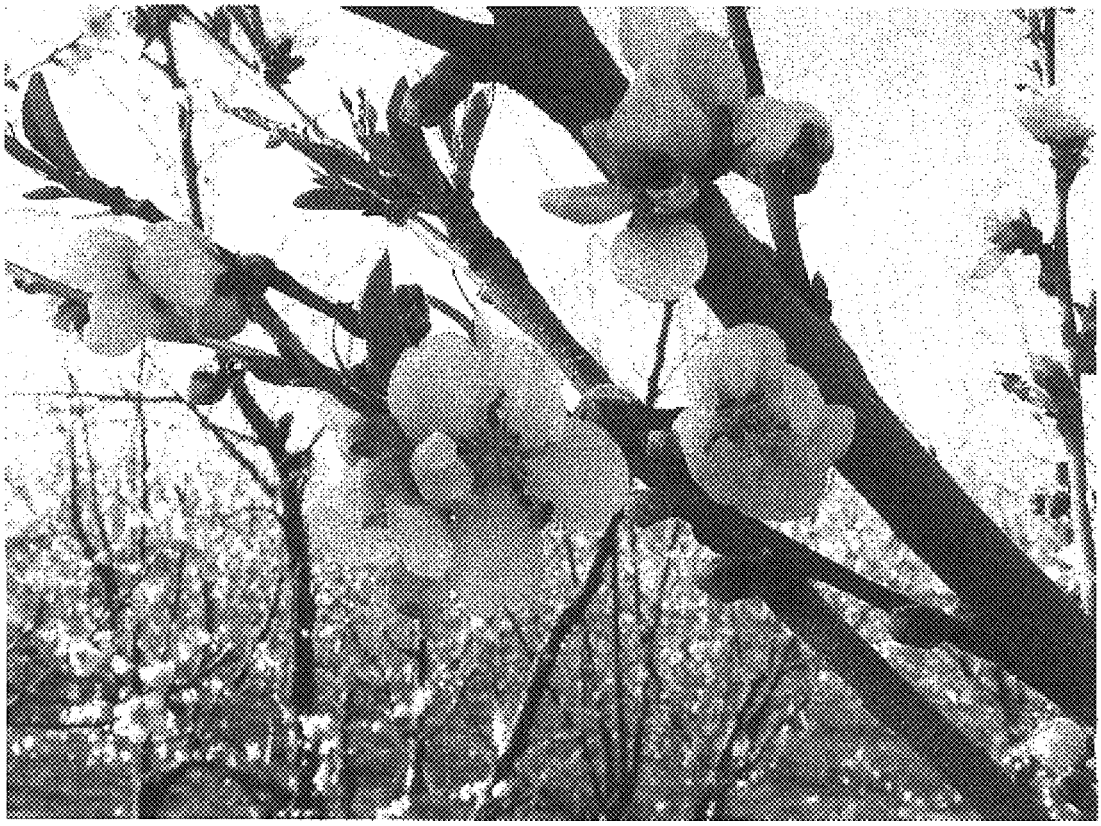
FIG. 2 shows branches and blossoms of the new cultivar.
Figure 3:
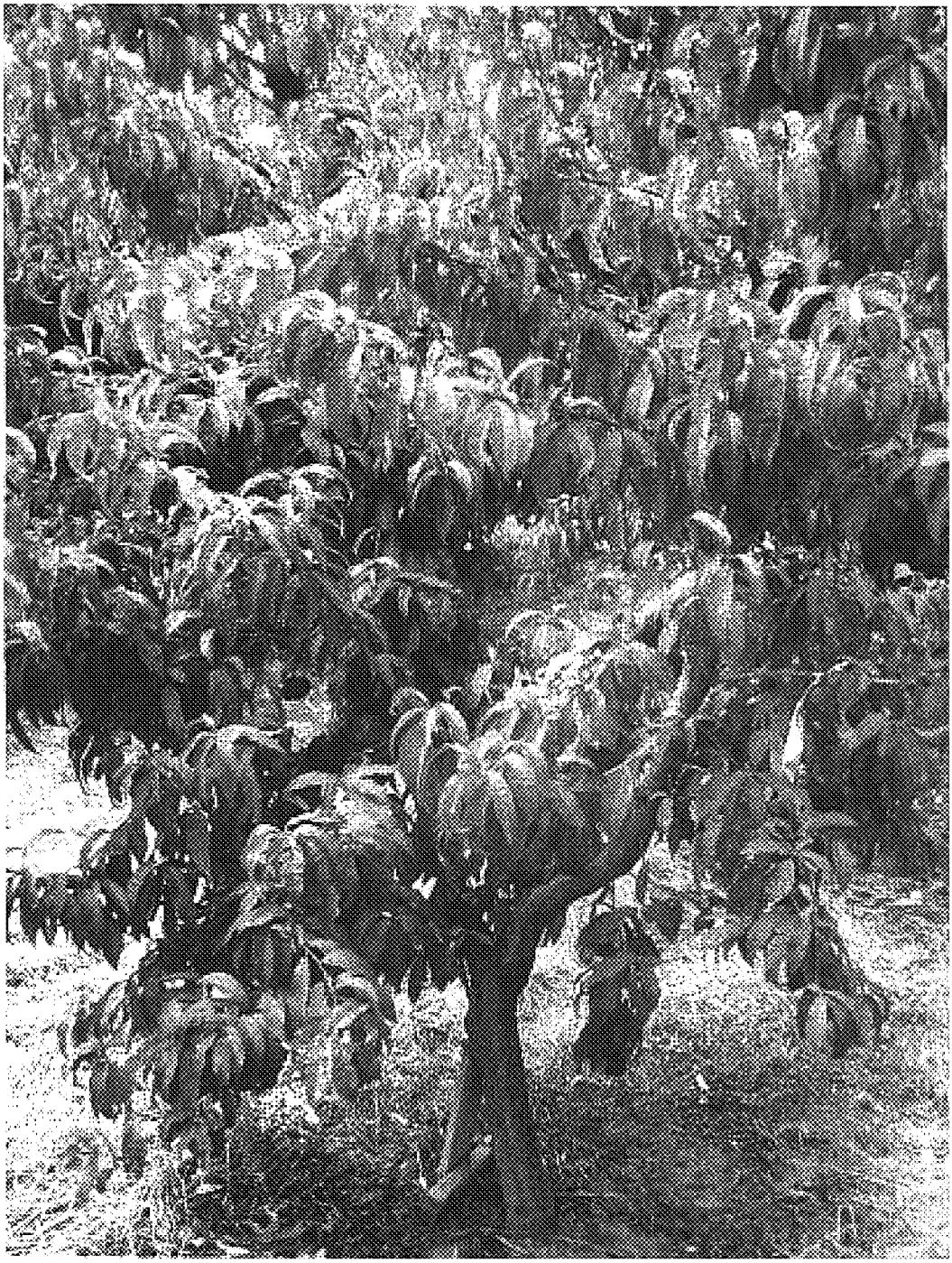
FIG. 3 shows a tree of the new cultivar.
Figure 4:
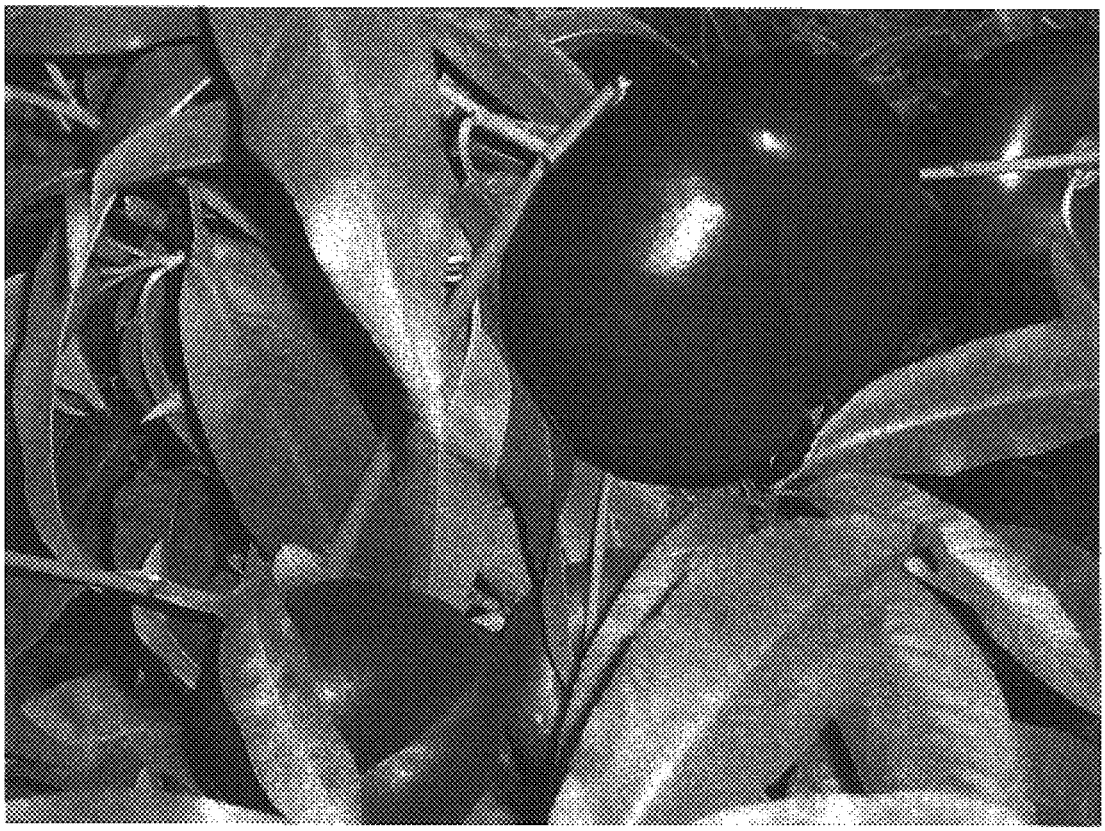
FIG. 4 shows fruit and leaves of the new cultivar.
Figure 5:
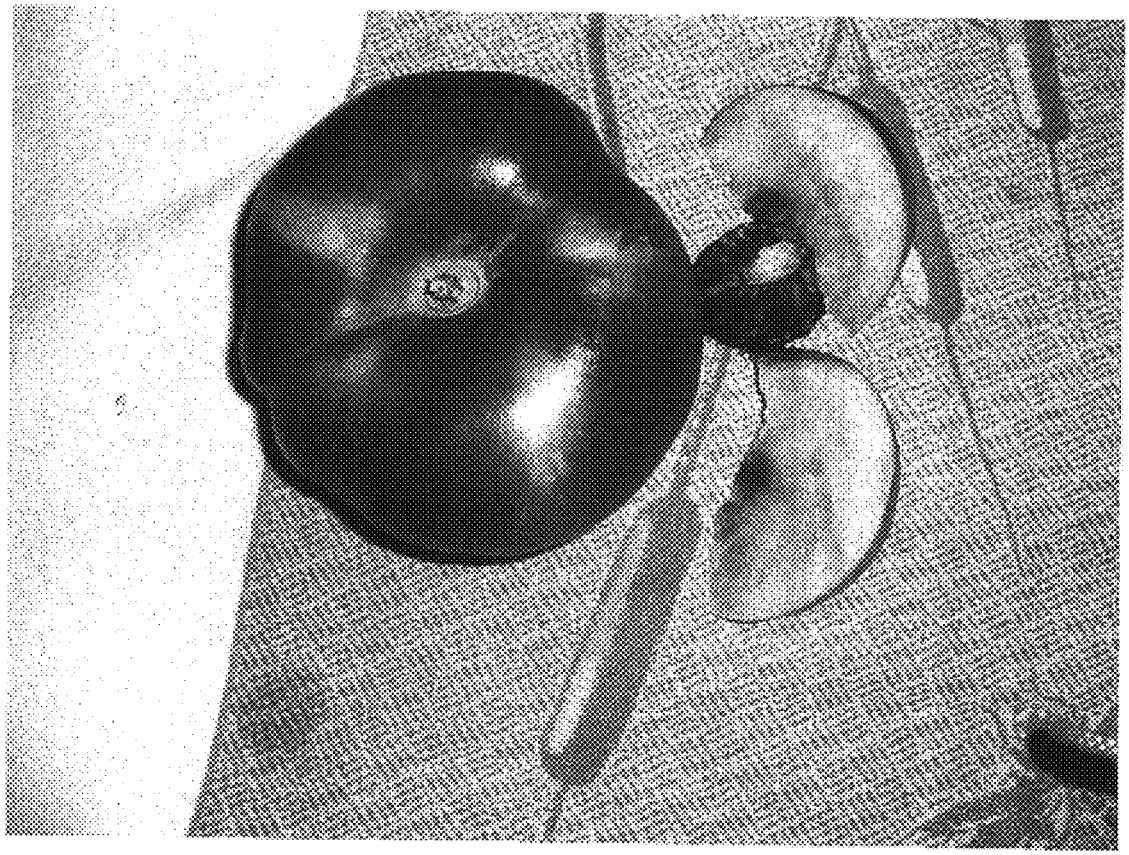
FIG. 5 shows a sectioned fruit of the new cultivar.

The following is a detailed botanical description of 'S 6817,' a new and distinct nectarine tree, based on observations made during the 2004 growing season, of specimens planted at Parker, Wash., USA, in 2001. The described trees were grown on 'Lovell' (not patented) rootstock. All colors are described according to The Royal Horticultural Society Colour Chart. It should be understood that the botanical and analytical characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Tree:

*Type.*—Non-spur type.
*Vigor.*—Strong.
*Habit.*—Upright, spreading.
*Size.*—Width 3.2 m; height 1.9 m.
*Trunk.*—Diameter 23.8 cm at soil level; bark very rough; overcolor grey 201D; undercolor grey-orange 166D; lenticels 0.4 to 0.6 cm, yellow 159A.

Flowering branch:

*Size.*—Lateral branch diameter 2.6 cm, length 40.4 cm (previous season growth); internode length 2.8 to 4.9 cm.

*Color.*—Greyed-red 178A.

*Anthocyanin coloration.*—Present, medium intensity, red-purple 60B.

Buds:

*Abundance of flower buds.*—Many.

*Distribution of flower buds.*—Generally in groups of two or more.

*Bud burst.*—March 20 at Parker, Wash.

*Duration of flowering.*—March 20 to April 7 at Parker, Wash.

*Bud size.*—Length 0.8 to 0.9 cm.

*Bud shape.*—Elongated with blunt tip, smooth.

*Bud color.*—Red-purple 60A, tip pink 68B.

*Tolerance to cold.*—Hardy.

Flower:

*Type.*—Showy.

*Calyx color* (*open flower before falling of petals*).—Orange.

*Petals.*—Quantity 5; length 1.6 to 1.7 cm, width 1.2 to 1.4 cm; margins ruffled, overlapping; shape rotund; color at tip pink 69C, at base pink 70B.

*Flower size.*—Diameter 3.9 to 4.0 cm.

*Fragrance.*—Mild.

*Sepals.*—Length 0.4 to 0.5 cm, width 0.3 to 0.4 cm; red-purple 60A.

*Reproductive organs.*—Stamen white 155D, quantity 32, length 0.9 to 1.0 cm; anther length 0.5 cm; filament 0.8 to 0.9 cm; pistil 1.1 to 1.2 cm, smooth, yellow 1A.

*Pollen.*—Semi-abundant, yellow 1A.

Leaves:

*Size.*—Large, length 14.5 cm, width 3.0 cm.

*Ratio length/width.*—Medium.

*Leaf shape.*—Oblanceolate, upfolded, tip recurved downward, base nearly right angle, equilateral, apex acuminate.

*Leaf margin.*—Serrulate.

*Leaf color.*—Upper surface green 147A; lower surface green 144A, anthocyanin coloration absent.

Petiole:

*Size.*—Length 1.0 cm, diameter 0.1 cm.

*Green.*—Green 149D.

*Glands.*—Present, usually more than 2, reniform.

Fruit:

*Size.*—Medium, diameter 8.6 cm.

*Shape in profile view.*—Oblate, very flat.

*Shape of tip.*—Bowl shaped depressed.

*Symmetry when cut along suture.*—Asymmetric.

*Suture.*—Marked.

*Depth of petiole cavity.*—Shallow, 1.2 cm.

*Width of petiole cavity.*—Medium, 4.0 cm.

*Skin.*—Thin, smooth, tenacious; ground color yellow-orange 19A, overcolor red 45A.

*Firmness of flesh.*—Firm, crisp.

*Flesh texture.*—Fine.

*Color.*—Yellow-orange 23C.

*Anthocyanin coloration directly under skin.*—Absent.

*Anthocyanin coloration of the flesh.*—Absent.

*Anthocyanin coloration around the stone.*—Present, red 43A.

*Pit cavity.*—Diameter 2.6 cm, color red-purple 59C.

*Flavor.*—Sub-acid.

*Sugar content of flesh.*—Medium, 12.5° Brix.

Stone:

*Size.*—Small in relation to fruit, diameter 26 mm.

*Shape.*—Flat, round, surface texture ridged.

*Color.*—Red, 53A.

*Likelihood of stone to split.*—Absent or very weak.

*Degree of adherence to flesh.*—Medium, semi-freestone.

Maturity:

*Time of maturity.*—Late, beginning August 27 at Parker, Wash.; requires more than one picking.

*Preharvest drop.*—Some occurrence.

Heat and cold tolerance: Tolerant in area tested (USDA Zone 6).

Resistance to diseases and pests: None observed.

We claim:

1. A new and disctinct nectarine tree, substantially as shown and described herein.

* * * * *

UNITED STATES PATENT AND TRADEMARK OFFICE

CERTIFICATE OF CORRECTION

PATENT NO. : PP 16,490 P2
APPLICATION NO. : 10/642441
DATED : May 2, 2006
INVENTOR(S) : Rene Francois Monet It is certified that error appears in the above-identified patent and that said Letters Patent is hereby corrected as shown below:

Column 1,
Line 11, "Independece" should read --Independence --; and

Column 4,
Line 3, "Green." should read --Color. --.

Signed and Sealed this

Twenty-second Day of August, 2006

JON W. DUDAS
*Director of the United States Patent and Trademark Office*